United States Patent [19]
Kuslich et al.

[11] Patent Number: 5,458,638
[45] Date of Patent: Oct. 17, 1995

[54] NON-THREADED SPINAL IMPLANT

[75] Inventors: Stephen D. Kuslich, Maplewood, Minn.; James D. Corin, Dublin, Ohio; George W. Bagby, Spokane, Wash.

[73] Assignee: Spine-Tech, Inc., Minneapolis, Minn.

[21] Appl. No.: 972,827

[22] Filed: Nov. 6, 1992

Related U.S. Application Data

[60] Division of Ser. No. 702,351, May 15, 1991, abandoned, which is a continuation-in-part of Ser. No. 405,564, Sep. 8, 1989, abandoned, which is a continuation-in-part of Ser. No. 376,657, Jul. 6, 1989, abandoned.

[51] Int. Cl.$^6$ ................................................. A61F 2/44
[52] U.S. Cl. ................................. 623/17; 606/61
[58] Field of Search ................. 623/16–18; 606/60–61

[56] References Cited

U.S. PATENT DOCUMENTS

| | | | |
|---|---|---|---|
| 4,349,921 | 9/1982 | Kuntz | 623/17 |
| 4,599,086 | 7/1986 | Doty | 623/17 |
| 4,834,757 | 5/1989 | Brantigan | 623/17 |
| 4,892,545 | 1/1990 | Day et al. | 623/17 |
| 4,904,261 | 2/1990 | Dove et al. | 623/17 |

*Primary Examiner*—David H. Willse
*Attorney, Agent, or Firm*—Merchant, Gould, Smith, Edell, Welter & Schmidt

[57] ABSTRACT

An implant is disclosed for use in spinal stabilization. In one preferred embodiment, the implant is a body having side walls extending between upper and lower walls with openings on the upper and lower walls. The side walls are solid and oppose disk material.

5 Claims, 8 Drawing Sheets

NON-THREADED SPINAL IMPLANT

CROSS-REFERENCE TO RELATED APPLICATION

The present application is a divisional application of Ser. No. 07/702,351, filed May 15, 1991, now abandoned, which is a continuation-in-part of U.S. Ser. No. 07/405,564, filed Sep. 8, 1989, now abandoned, which is a continuation-in-part application claiming priority to commonly assigned U.S. patent application Ser. No. 07/376,657, filed Jul. 6, 1989, entitled "Spinal Prosthesis", now abandoned, and naming the same inventors as the present invention.

BACKGROUND OF THE INVENTION

1. Field of the Invention

This invention pertains to surgical procedures for stabilizing the spine. More particularly, this invention pertains to a novel implant for use in such a procedure.

2. Description of the Prior Art

Chronic low back pain is one of the most common and perplexing problems facing the field of orthopedic surgery. In addition to patient discomfort, chronic low back pain has severe adverse societal impacts including lost income, possible chronic dependence on drugs, alcohol and public relief programs.

In many cases, low back pain can be avoided by preventing relative motion between spinal vertebrae (commonly referred to as intervertebral stabilization). To abate low back pain, stabilization is directed to stabilizing contiguous vertebrae in the lumbar region of the spine.

Surgical techniques are known for use in spinal stabilization. Surgical techniques seek to rigidly join vertebrae which are separated by a degenerated disk. Ideally, the surgery effectively replaces the vertebra-disk-vertebra combination with a single rigid vertebra. Various surgical techniques have developed which attempt to approach or approximate this ideal.

One technique known in the art is to partially remove a degenerated disk and to insert a bone graft into the void formed by the removed disk. Other techniques involve the use of an implant which, acting alone or in combination with bone fragments, replace the use of bone grafts. An example of such implant is shown in U.S. Pat. No. 4,501,269 to Bagby dated Feb. 26, 1985. In Bagby, a large, cylindrical basket is driven into a hole formed between bones which are to be joined. The basket is hollow and is filled with bone fragments which are produced during a boring step. Bone-to-bone fusion is achieved through and about the basket. In Bagby, the hole for the Basket is slightly smaller than the diameter of the basket. This structure results in the spreading of the opposing bone segments upon insertion of the basket. This results in taughtness, which provides initial stabilization. Eventual fusion of the opposing bone segments results from bone growth through the basket.

Prostheses such as that shown in U.S. Pat. No. 4,501,269 are promising. However, improved implant design is necessary to enhance patient safety and the probability of a satisfactory recovery.

SUMMARY OF THE INVENTION

According to a preferred embodiment of the present invention, an implant is disclosed for insertion into a body formed between opposing vertebrae of an animal's spine. The implant includes a rigid body having a leading end and a trailing end spaced apart along a longitudinal axis of the body. The body has side walls extending between upper and lower walls. The body defines a chamber which is exposed through the body by openings extending through the upper and lower walls. The chamber may be filled with bone fragments which can fuse with the vertebra bone material through the openings.

In an alternative embodiment of the invention disclosed herein, a generally oval-shaped implant is disclosed which is hammered into an elongated bore between two opposing vertebrae. The oval-shaped implant has enhanced surface area contact between the vertebrae and provides greater integrity against rotational motion between opposing vertebrae.

DESCRIPTION OF THE PREFERRED EMBODIMENT

A. General

Figure 1:
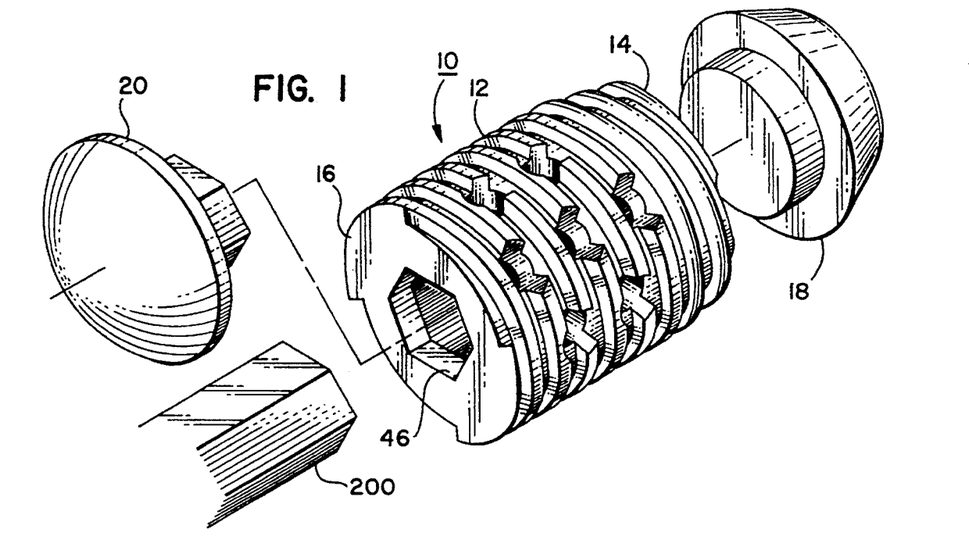
FIG. 1 is a perspective exploded of view of an implant according to a preferred embodiment of the present invention.
Figure 12:
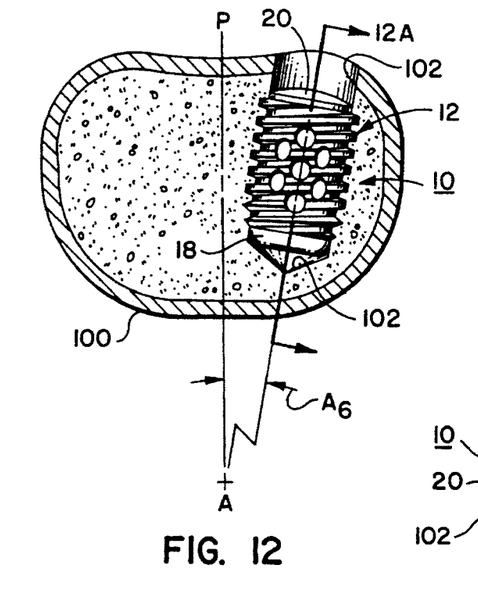
FIG. 12 is a top plan view showing insertion of a single implant of FIG. 1 into an intervertebral space.

Reference is now directed to FIGS. 1 and 12. FIG. 1 is an exploded perspective view of an implant according to a preferred embodiment of the present invention. The implant is shown generally at 10. FIG. 12 shows the implant 10 inserted within a bore 102 formed in a human vertebra body 100.

For ease of description, the implant 10 (as well as alternative embodiments of the invention) will be described for use in a human spine. Further, dimensions, when given, will be preferred dimensions for use in a specific spinal location of a particular class of humans— notably, the L-5 vertebra of a typical adult male. It will be appreciated that the present invention is intended for use in a wide variety of vertebra sizes and a wide variety of animal species. The dimensions of the implant 10 (as well as the dimensions of the alternative embodiments) will vary necessarily with the size of the vertebra in which the implant 10 is to be used. However, making variations to the dimensions and sizes in order to accommodate differing sizes of vertebrae will be well within the skill of the art.

B. First Preferred Embodiment

With reference now directed to FIGS. 1–12, a first preferred embodiment of the present invention will now be described. Identical elements are numbered identically throughout.

The implant 10 includes a body 12 (shown separately in FIGS. 2, 3–6) having a leading end 14 and a trailing end 16 which are spaced apart along a longitudinal axis X-X of the body 12. The implant also includes a leading end cap 18 and a trailing end cap 20 (shown separately in FIGS. 8–9 and FIGS. 10–11, respectively).

Body 12 is integrally constructed from a rigid, biocompatible material. While any rigid, biocompatible material (such as a ceramic) could be used, body 12 is preferably formed from titanium and/or its alloys. Titanium and/or its alloys is preferred since it is noncorrosive and fatigue resistent. Also, titanium is widely used in prosthetic devices and the material has a proven record of satisfactory performance.

Figure 3:
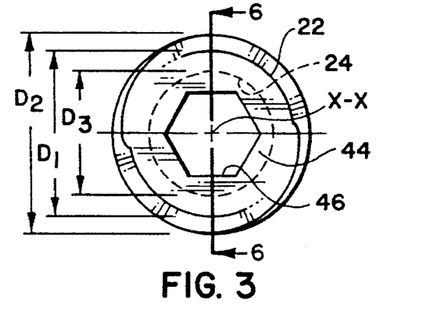
FIG. 3 is an end view taken in elevation of the trailing end of the body portion of FIG. 2 taken along line 3—3 of FIG. 2.

With best reference to FIGS. 2–7 and 7A, the body 12 includes a hollow cylindrical shell 22 of predetermined diameter $D_1$ (see FIG. 3). For reasons that will be later described $D_1$ is selected to be about 0.5 inches.

The shell 22 surrounds and defines an interior chamber 24. Chamber 24 has a diameter $D_3$ of preferably about 0.384 inches.

Threads 26 and 28 are formed on the exterior surface of shell 22 spirally wound around shell 22 and integral therewith. While double threading is shown, single threading or multiple threading in excess of double threading could be applied. Threads 26, 28 are disposed and selected for the threads 26, 28 to engage the bone material of opposing vertebrae and draw the body 12 in the direction of axis X-X upon rotation of the body 12 about axis X-X.

In a preferred embodiment, body 12 is self-tapping. Mainly, the threading 26, 28 (see FIG. 2) adjacent leading end 14 is tapered as shown by angle $A_1$ (which is preferably about 15°, see FIG. 2). Away from the tapered end 14, and adjacent the trailing end 16, the threads 26, 28 present flat, annular surfaces 30 which are in alignment and parallel to shell 22. Accordingly, the thread profile presents a generally bullet-shaped profile which is cylindrical along the majority of the body 12 and tapers inwardly toward axis X-X at the leading end 14.

The tapered portion of body 12 preferably has a length $L_1$ of about 0.198 inches. The overall length of body 12, $L_2$, is preferably about 0.740 inches. (See FIG. 2).

Figure 7:
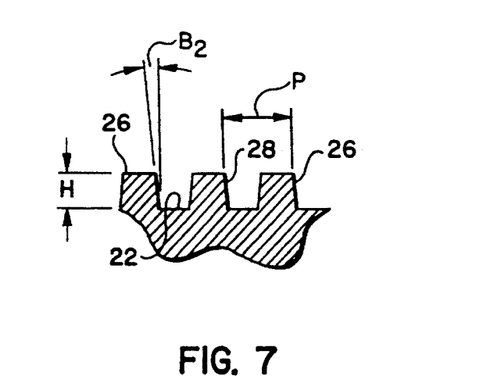
FIG. 7 is an enlarged view, taken in section, of the threads of the body of FIG. 2 adjacent the trailing end.
Figure 7A:
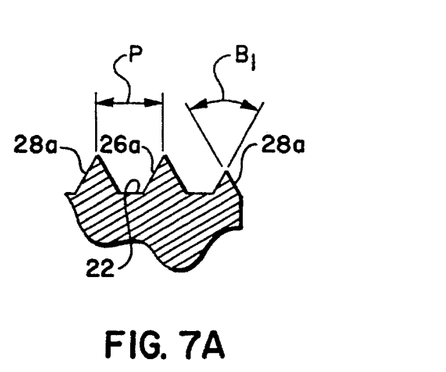
FIG. 7A is a view, taken in section, of the threads of the body portion of FIG. 2 adjacent a leading end of the body.
Figure 8:
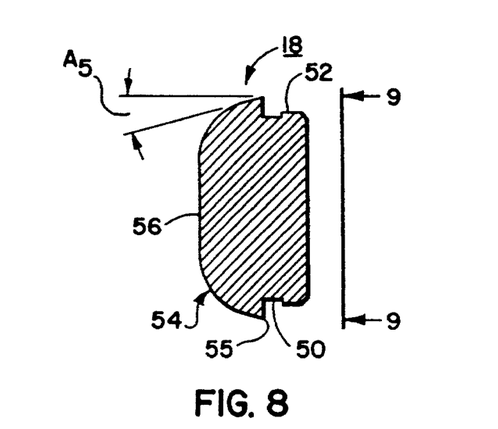
FIG. 8 is a side sectional view of a leading end cap of the implant of FIG. 1.
Figure 9:
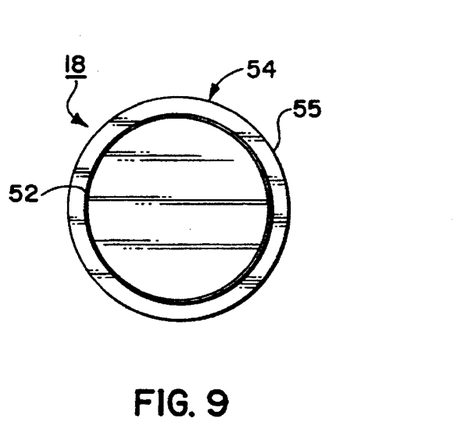
FIG. 9 is an inside end elevation view of the end cap of FIG. 8 taken along line 9—9 of FIG. 8.
Figure 10:
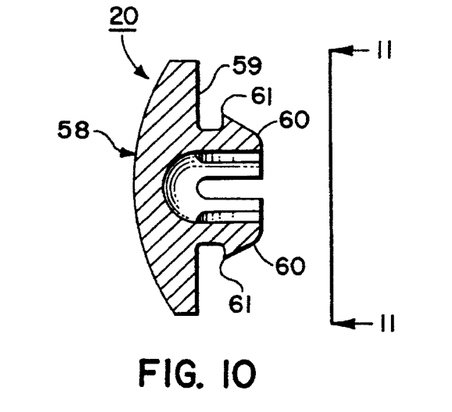
FIG. 10 is a side sectional view of a trailing end cap of the implant of FIG. 1.
Figure 11:
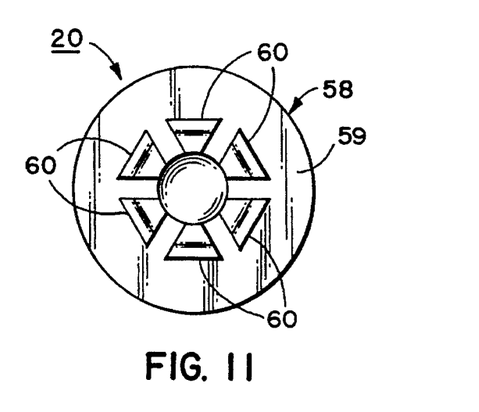
FIG. 11 is an end elevation view of the end cap of FIG. 10 taken along line 11—11 of FIG. 10.

To assist in the self-tapping, the threads 26, 28 experience a change in profile from the leading end 14 to the trailing end 16. At the leading end 14, the threads are sharp, as shown in FIG. 7A. When the taper portion of body 12 is passed, the threads 26, 28 assume a profile which is generally rectangular as shown in FIG. 7. For ease of discussion, the sharp portions of threads 26, 28 are numbered 26a, 28a in the drawings.

The changing thread profiles are selected to assist in advancing the implant 10 into an intervertebral space and to a hold the implant 10 securely in place when fully advanced. The sharp portion of threads 26, 28 (thread portions 26a, 28a shown in FIG. 7A) cut bone better and assist in advancing the implant 10. The generally rectangular thread profile (FIG. 7) has greater cross-sectional area and better opposes bone surfaces to hold the implant 10 in place.

Preferred dimensions of the threading 26, 28 are shown in FIGS. 7 and 7A with a pitch, P, (distance between opposing threads) equaling about 0.10 inch for both the rectangular and sharp threading of FIGS. 7 and 7A. The bevel $B_1$, of the sharp threading (FIG. 7A) is preferably about 57°. The bevel, $B_2$, of the rectangular thread portion (FIG. 7) is preferably about 5°. The height, H, of the rectangular thread is about 0.10 inches. This, together with the diameter $D_1$ (see FIG. 3) of the shell 22 results in overall diameter of the body 12 being about 0.6 inches. It will be appreciated that these dimensions as well as remaining dimensions given throughout this application are preferred dimensions and may be varied while retaining the structure and function of the present invention. The scope of the claims of the present invention is not intended to be limited by dimensions which are set forth only to illustrate a preferred embodiment.

The body 12 has a plurality of holes 32 formed radially through the shell 22 and threads 26, 28. The holes 32 provide communication between interior chamber 24 and an exterior of the body 12.

The holes 32 are identical and each is preferably about 0.125 inches in diameter. Shown best in FIG. 4, each of the holes 32 includes a countersunk portion 34 at the radially outer surface of threads 26, 28. Preferably, the countersunk portion 34 has a diameter of about 0.155 inches.

Figure 6:
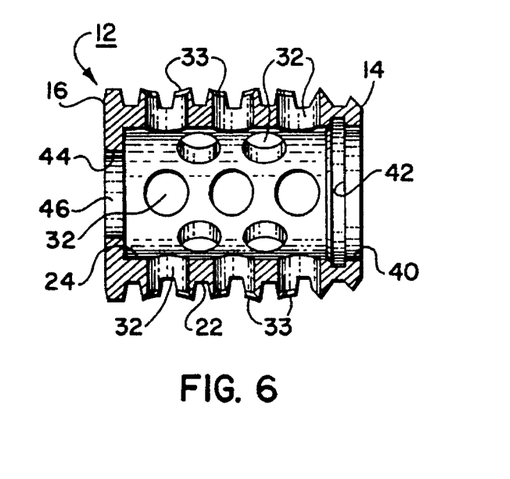
FIG. 6 is a view taken along lines 6—6 of FIG. 3.

The countersunk portion 34 creates cutting a beveled edge 33 on the rectangular threads 26, 28 in the location of the holes 32. This cutting edge 33 is best shown in FIG. 6. The cutting edges 33 chip away bone as the body 12 is rotated. The bone chips will migrate through the holes 32 into chamber 24. As will be described, it is anticipated that this chipping action will enhance the bone-to-bone fusion sought with the present invention.

Figure 5:
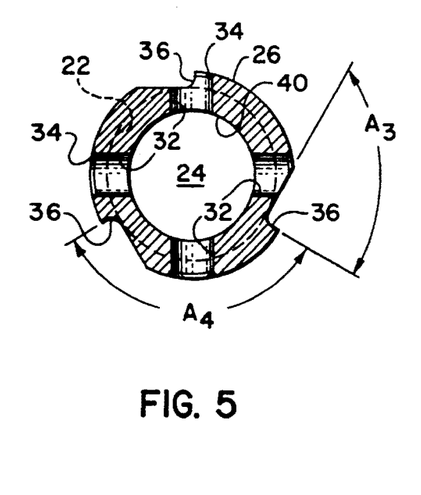
FIG. 5 is a view taken along line 5—5 of FIG. 2.

In the region of the self-tapping sharp threads 26a, 28a (FIG. 7A), the threads 26a, 28a are shown self-tapping in FIG. 5 to present self-tapping cutting edges 36 set at a 90° cutting angle $A_3$. The cutting edges 36 are shown spaced apart by an angle $A_4$ of about 120°.

In the preferred embodiment as shown, holes 32 extend through the threads 26 and 28. An alternative embodiment would have the threads 26 and 28 spaced apart a distance greater than that shown in the present drawings, with the holes 32 extending through the shell 22 and not passing through threads 26 and 28. Such a design presents enhanced structural integrity since the more massive threads 26 and 28 are not being broken. However, such an alternative design forgoes the anticipated benefits which may be attributed to the chipping action of the cutting edges 33 of the threads adjacent holes 32.

The number of holes 32 in the body 12 as shown is twenty. This number may vary. The number is selected to be as many and as large as possible (to enhance bone fusion), while not compromising the strength of the body 12.

As previously indicated, the body 12 extends from a leading end 14 to a trailing end 16. Leading end 14 has a circular axial opening 40 formed therethrough in communication with chamber 24. Disposed inwardly from leading end 14 is an annular groove 42 (see FIG. 6) provided to facilitate attachment of leading end cap 18 as will be described.

Trailing end 16 has an inwardly projecting flange 44. Opposing surfaces of flange 44 define a centrally located hexagon-shaped axial opening 46.

When the implant 10 is in place in an intervertebral space, circular axial opening 40 and hexagon axial opening 46 are covered by caps 18 and 20. Shown best in FIGS. 8 and 9, the leading end cap 18 includes a cylindrical hub portion 50 and an annular flange 52 extending from hub portion 50. Also extending from hub portion 50 on the side opposite flange 52 is a tapered cap portion 54 which extends from a large diameter 55 and tapers inwardly to a smaller diameter terminal end 56. An angle of taper $A_5$ (FIG. 8) is preferably about 15° to correspond with the angle of taper $A_1$ (FIG. 2) of body 12. The large diameter 55 is preferably selected to equal the diameter of body 12 at leading end 14. Flange 52 is selected to be snap received into annular groove 42. So received, cap 18 is permanently attached to the leading end 14 covering axial opening 40.

Trailing end cover 20 (FIGS. 10 and 11) includes an arcuate cap 58 sized to cover end 16 with a flat surface portion 59 of cap 20 abutting trailing end 16. Six flexible retaining clips 60 are provided centrally extending from surface 59. Clips 60 are sized to be snap received within hexagon-shaped opening 46. Accordingly, the cooperation of surface 59 and the barbed portion 61 of clips 60 capture flange 44 to thereby hold trailing end cap 20 securely against trailing end 16. For reasons that will be described, each of caps 18 and 20 are preferably formed from high-density polyethylene.

C. Method of Use

Figure 12A:
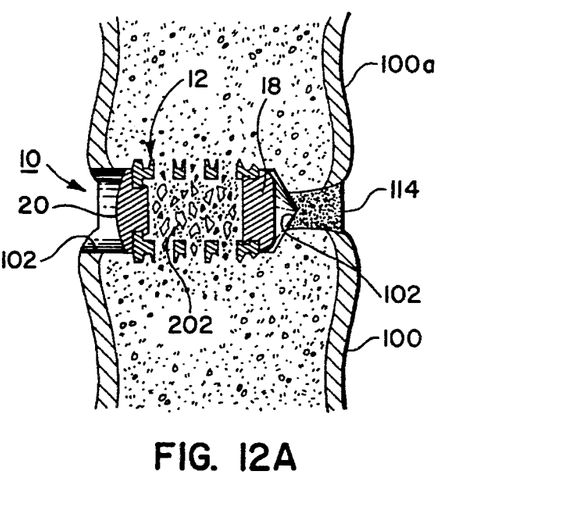
FIG. 12A is a view taken along lines 12A—12A of FIG. 12.

Referring to FIGS. 12 and 12A, the method of use of the implant 10 will now be described. In use of the implant 10, a surgeon forms a bore 102 through the intervertebral space in a disk 114 separating two opposing vertebral bodies 100 and 100a. The bore 102 is sized to be as large as possible to remove disk material 114 and to at least partially cut into opposing surfaces of the bone of vertebra bodies 100, 100a. It will be appreciated that it is well within the skill of the art to form bores such as bore 102.

FIG. 12 and 12A show a bore 102 formed through a posterior approach through a spine. In a posterior approach, a surgeon approaches the vertebra through the back of the patient. Preferably, the axis of the bore 102 is formed an angle with the anterior-posterior axis, A-P, of the vertebra body 100, 100a. As shown in the preferred surgical approach, the angle $A_6$ between the A-P axis and the bore axis is about 10°.

It is recognized that there are limits on the maximum size of a bore 102 that can directly drilled in a vertebra body via a posterior approach. Limitations on the diameter of the bore 102 include location of important nerves and blood vessels which can be damaged by excessively large bore drilling operations. The maximum size bore that can be cut will depend on the particular location of the spine, the species of the animal, age and sex. A common safe maximum for an adult male spine in the L-5 area would be a bore diameter of about 0.5 inches.

For reasons that will be described, it is preferred that the bore diameter will be smaller than the diameter, $D_1$, of body shell 22. Specifically, it is anticipated that a bore diameter of about 3 millimeters less than diameter $D_1$ will be preferred. With such structure, the body 12 spreads apart opposing vertebrae upon insertion. By virtue of the spreading effect, the disk annulus becomes taught, thereby providing for the initial stabilization between the opposing vertebrae. (Those skilled in the art will recognize the annulus as being the fibrous outer circumferential portion of the disk). In the drawings, the implant is shown spreading apart the vertebrae and stretching the annulus. Eventual fusion of the opposing vertebrae results from bone growth through body 12, as will be described.

The implant 10 is partially assembled with leading end cap 18 snapped onto leading end 14. With trailing end cap 20 removed, the implant 10 is partially placed within bore 102 with the tapered leading end 14 received within bore 102. An advancing tool (the tip of which is shown in FIG. 1) is provided having a hexagon-shaped tip 200 complementarily sized to be received within opening 46. The tip 200 is inserted by the surgeon into opening 46. The surgeon then turns the tool and, hence, the body 12, in a clockwise direction (from the perspective of the surgeon). The turning action of the body 12 causes the sharp threads 26a, 28a (FIG. 7A) to cut into the bone of the opposing vertebrae bodies 100, 100a to advance the body 12 into bore 102 to the fully inserted position shown in FIG. 12. The rectangular threads 26, 28 (FIG. 7) retain the body 12 in the desired axial position relative to bore 102. Leading end cap 18 covering axial opening 40 prevents disk material from migrating through axial opening 40 into chamber 24 during insertion of implant 10 as well as during the patient's recovery phase.

With the implant body 12 fully inserted as shown in FIG. 12, the trailing end cap 18 has not yet been installed. Accordingly, axial opening 46 exposes chamber 24 to the surgeon once the tool tip 200 is removed. With opening 46 still exposing chamber 24, a surgeon can impact a graft medium 202 (preferably bone chips) into chamber 24 (see FIG. 12A). Any impacted bone chips will supplement bone chips that may migrate through holes 32 as a result of the cutting action of cutting edges 33 against the vertebra bone surfaces.

With the graft medium fully applied to chamber 24, the surgeon snaps cap 20 into hole 46 to cover the trailing end 16. FIGS. 12 and 12A show such a fully assembled and inserted implant 10. The surgeon can then close the patient through any suitable technique. With the completed implant 10 installed in the manner indicated, the bone graft 202 within chamber 24 and openings 32 fuses together with the bone of the opposing vertebrae 100, 100a to thereby join the vertebrae 100, 100a together.

As previously indicated, end caps 18, 20 are preferably formed from high density polyethylene. Such material is nonabrasive and inert, and has a slippery touch. This latter feature is particularly valuable for trailing end cap 20, which may oppose the epidural tissue. To avoid damage or irritation of the dura, the slippery, inert, nonabrasive polyurethane trailing end cap 20 is provided. Trailing end cap 20 is intended to cover axial opening 46 and retain the bone chips within chamber 24 while providing a nonabrasive and nonirritating surface opposing the epidura. Also, like leading end cap 18, trailing end cap 20 prevents disk material from entering chamber 24.

In a preferred embodiment, the end caps 18, 20 formed of polyethylene which is radiolucent. Radiolucent material permits X-rays to pass. Accordingly, with radiolucent end caps 18, 20, an attending physician can study the growth of bone within chamber 24 without the need for exploratory surgery.

Figure 2:
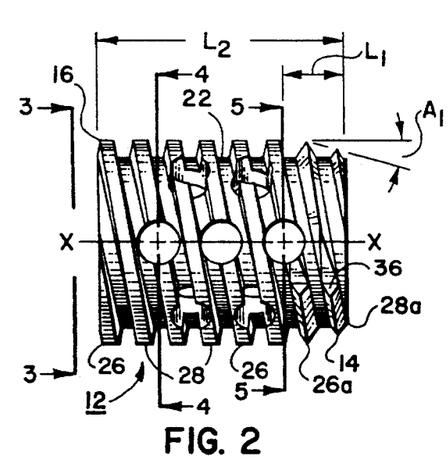
FIG. 2 is a side elevation view of a body portion of the implant of FIG. 1.
Figure 2A:
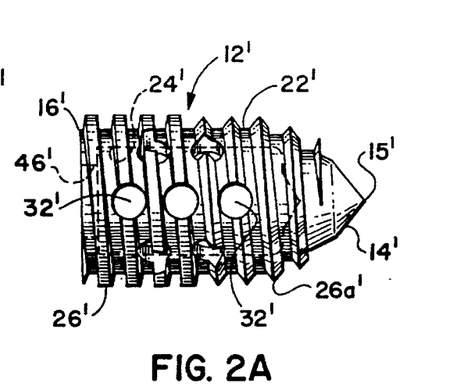
FIG. 2A is a side elevation view of an alternative embodiment of a body portion of an implant according to the present invention.

It will be appreciated that radiolucent end cap 18, 20, while desirable in a preferred embodiment, are not necessary to the practice of the full scope of the present invention. For example, the leading end 14 could taper completely as an integral portion of the solid body 12 as shown in FIG. 2A. In such an embodiment, the body 12' assumes a more complete hollow bullet-shaped profile where the leading edge 14' includes a sharp point 15' to better assist the insertion and advancement of the body 12' into the intervertebral space.

In FIGS. 12 and 12A, the implant 10 is shown installed on the left side (from the patient's perspective) of the anterior-posterior axis, A-P. For a posterior approach as shown in FIG. 12, it is anticipated that two prostheses 10 will be used, with a second implant disposed on the right side of the anterior-posterior axis, A-P, and installed in a manner identical to that of implant 10 on the left side. However, for ease of illustration, the right side implant is not shown installed. When installed, such prostheses would be positioned with the right and left prostheses being symmetrically disposed about axis A-P.

D. Alternative Design

Figure 3A:
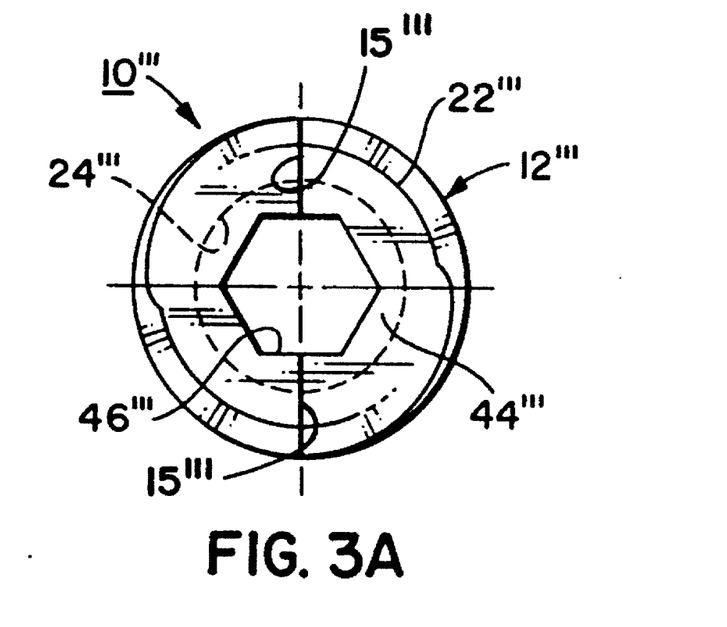
FIG. 3A is the same view as FIG. 3 showing an alternative embodiment.
Figure 4:
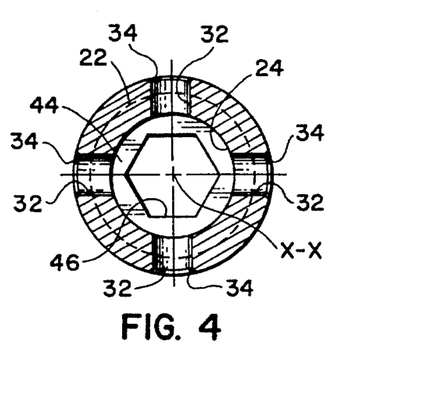
FIG. 4 is a view taken along lines 4—4 of FIG. 2.
Figure 4A:
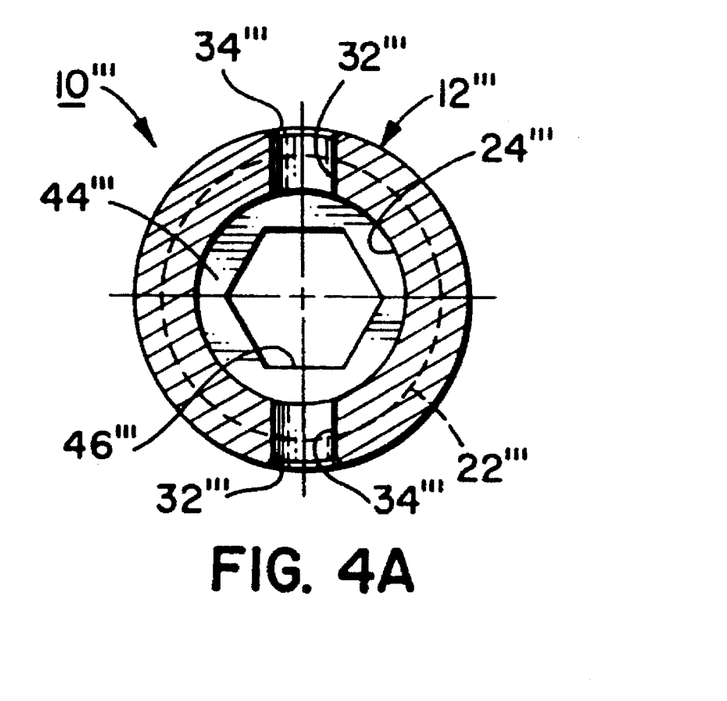
FIG. 4A is the same view as FIG. 4 showing an alternative embodiment.

FIGS. 3A and 4A show an alternative. The implant 10''' of the embodiment of FIGS. 3A and 4A is identical to that discussed above except as to the placement of holes 32'''. For ease of understanding the comparison between implant 10''' and implant 10, the reader will note that FIGS. 3A and 4A are the same view of implant 10''' as FIGS. 3 and 4 are of implant 10. Since the elements of the implant 10''' shown in FIGS. 3A and 4A are the same (except as will be described) as those shown in FIGS. 3 and 4, all similar elements are numbered identically except for the addition of the triple prime (''').

Unlike implant 10, implant 10''' does not have holes 32''' circumferentially spaced about body 12'''. Instead, as best shown in FIG. 4A, holes 32''' are placed on diametrically opposed sides of body 12'''.

Upon insertion of the implant 10''', the surgeon positions the implant 10''' with holes 32''' opposing the bone material of the vertebra bodies 100, 100a. As a result, no disc material 114 may enter into chamber 24'''. This prevents possible interference of disc material with the bone fusion process.

To assist a surgeon, indicia markings 15''' are placed on flange 44'''. The markings 15''' are aligned with the axis of holes 32'''. The surgeon turns body 12''' into position until markings 15''' are aligned pointing to bodies 100, 100a. So positioned, the surgeon knows the holes 32''' are opposing bone and not disc material.

E. Alternative Method and Apparatus for Anterior Approach

Figure 13:
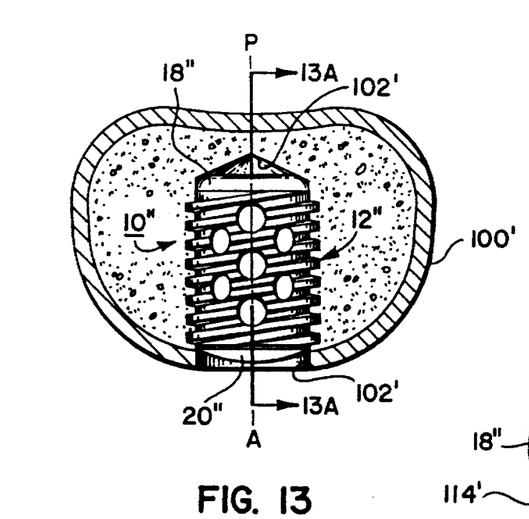
FIG. 13 is a top plan view showing an alternative embodiment of the present invention in place in a vertebra.
Figure 13A:
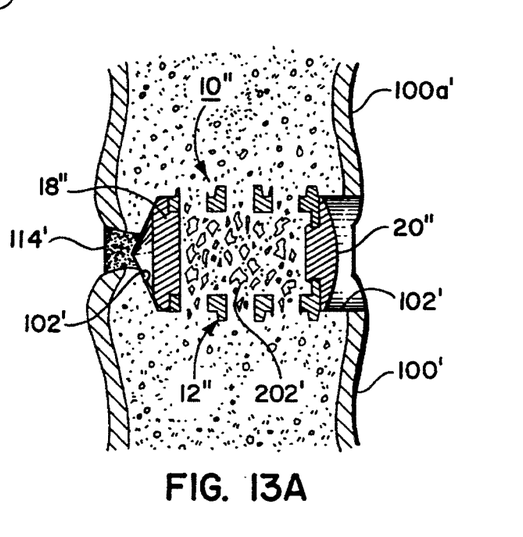
FIG. 13A is a view taken along lines 13A—13A of FIG. 13.

The foregoing description and illustration describe the insertion of an implant 10 through a posterior approach. FIGS. 13 and 13A show an alternative embodiment of the invention for use in an anterior approach where a bore 102' is formed from the front of the spine and axially aligned with the anterior-posterior axis, A-P. Since the bore 102' is formed from an anterior approach, the size restrictions of a posteriorly formed bore (namely, locations of nerves and blood vessels) are largely avoided. As a result, a large diameter bore 102' can be formed. A comparison of FIGS. 12A and 13A show the relative increase of bore diameter. This increase results in an enhanced surface area of exposed vertebra bone and an increased amount of graft material in an implant.

The implant 10'' shown in FIGS. 13 and 13A may be identical in proportional dimensions to that of implant 10, only enlarged to be received within the larger bore 102'. However, the implant 10'' shown in FIGS. 13 and 13A differs from that shown in FIGS. 12 and 12A. Namely, the implant 10'' shown in FIGS. 13 and 13A does not include a tapered leading end. Instead, the entire implant body 12'' is cylindrical-shaped to illustrate that, while a tapered leading end is preferred, it is not necessary to practice the teachings of the present invention.

F. Further Alternative Embodiments

Figure 14:
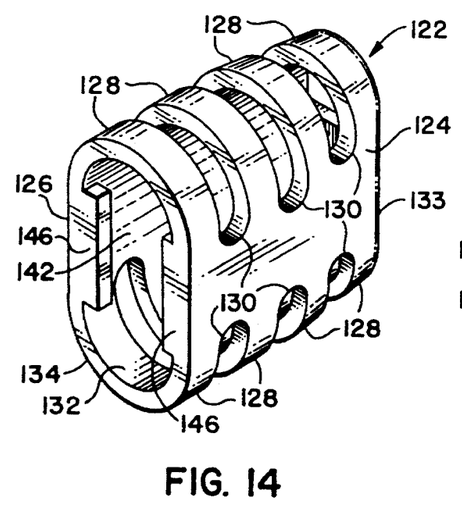
FIG. 14 is a perspective view of an alternative embodiment of the present invention showing an implant body leading end, side and top.
Figure 15:
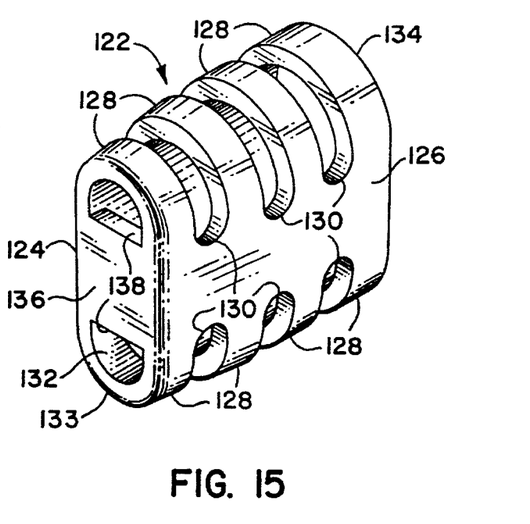
FIG. 15 is a perspective view of the body of FIG. 14 showing a trailing end, side and top.

FIGS. 15–25 illustrate yet a further embodiment of an implant for use in spinal stabilization. As shown in those figures, the implant 120 (shown assembled in FIGS. 23 and 25) includes a body portion 122 (shown in perspective in FIGS. 14 and 15) which is generally oval-shaped in cross section and formed from rigid, biocompatible material (preferably titanium). The body 122 includes generally flat side walls 124, 126 joined by upper and lower semi-cylindrical arcuate ribs 128. Arcuate ribs 128 are spaced apart to define a plurality of upper and lower semicircular arcuate openings 130 which provide communication between a hollow interior 132 of body 122 and an exterior. The ribs 128 define upper and lower walls of the implant 120 with the walls having openings 130 therethrough.

Body 122 extends from a leading or anterior end 133, and a trailing or posterior end 134. Anterior end 133 has a centrally positioned cover plate 136 which partially covers end 132 but leaves upper and lower semi-circular axial openings 138 exposing interior 132 through end 133.

Figure 16:
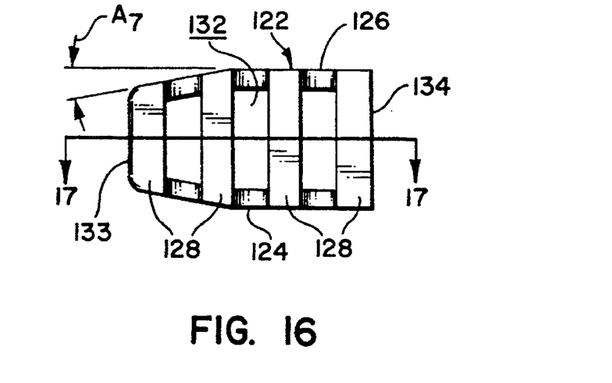
FIG. 16 is a top plan view of the embodiment of FIGS. 14 and 15.
Figure 17:
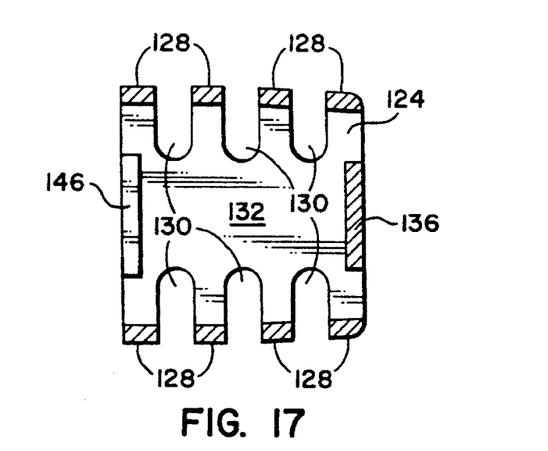
FIG. 17 is a side sectional view taken along lines 17—17 of FIG. 16.
Figure 18:
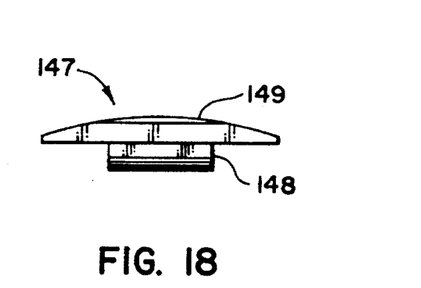
FIG. 18 is a side elevation view of a trailing end cap for use with the embodiment of FIGS. 14 and 15.
Figure 19:
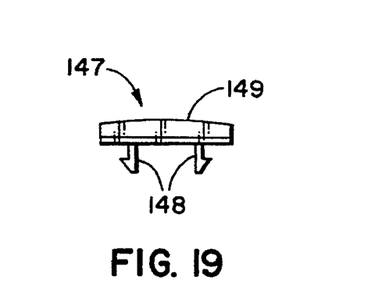
FIG. 19 is an end view taken in elevation of the end cap of FIG. 18.
Figure 20:
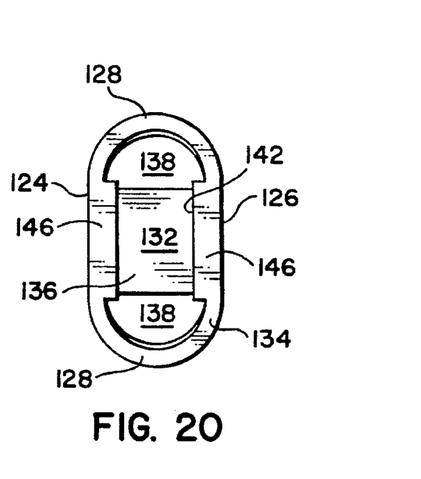
FIG. 20 is an elevation view a trailing end of the embodiment of FIGS. 14 and 15.
Figure 21:
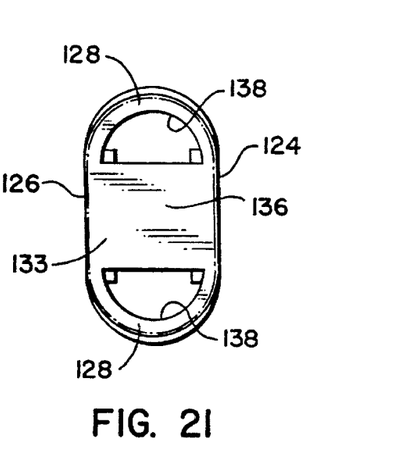
FIG. 21 is an elevation view of a leading end of the body of the embodiment of FIGS. 14 and 15.
Figure 22:
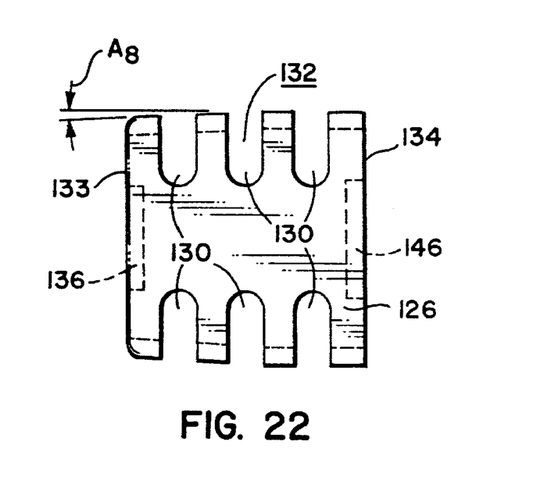
FIG. 22 is a side elevation view of the body portion of FIGS. 14 and 15.

Shown best in FIG. 16, body 122 is tapered at the leading end 133, with the side walls 124, 126 tapering inwardly at an angle $A_7$ of preferably 10° each. Also, the upper and lower planar of the ribs 128 are tapered inwardly as best shown in FIG. 22 at a preferred taper angles, $A_s$, of about 3°. The edges defined by the juncture of walls 124, 126, ribs 128 and end 133 are rounded to facilitate insertion of implant 120 as will be described.

The posterior end 134 (shown in FIG. 14) has an axial opening 142 which communicates with the body interior 132. A pair of opposing retaining ribs 146 are shown partially extending from the side walls 124, 126 into opening 142. A posterior end cap 147 is provided with an arcuate, smooth cap 149 sized to cover end 134 and opening 142. End cap 147 has retaining clips 148 selected to snap behind ribs 146 to thereby attach cap 147 against end 144.

G. Method of Use of Alternative Embodiment

Implant 120 is intended for use in a posterior approach with two prostheses 120 being inserted on opposite sides of the anterior-posterior axis of a vertebra. For ease of illustration, only one prosthetic device is shown inserted in FIGS. 23–25.

Figure 24:
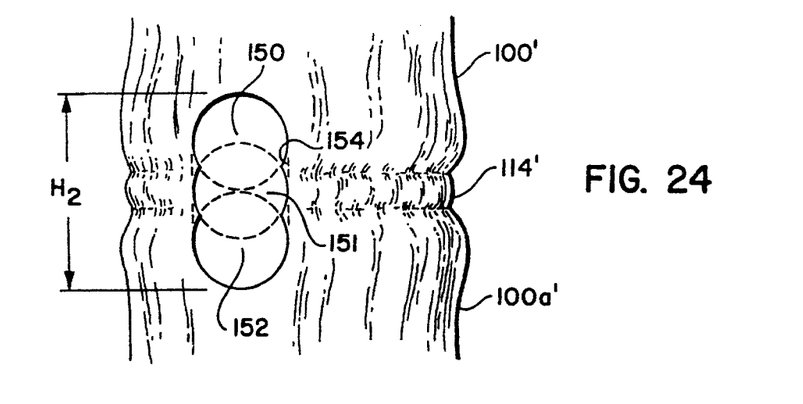
FIG. 24 is an anterior elevation view showing a bore drilling sequence prior to insertion of the implant as shown in FIG. 23.

FIG. 24 shows a method for drilling the bore 154 to receive the oval-shaped implant 120. As shown in FIG. 24, three circular bores 150, 151, 152 are drilled in vertical alignment in opposing vertebra bodies 100', 100a' and separating disk 114'. The three bores 150, 151, 152 cooperate to form a generally oval-shaped bore 154.

Figure 23:
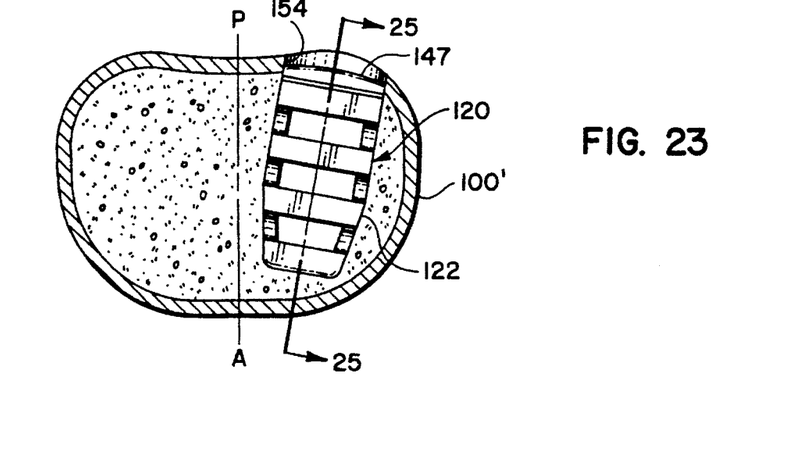
FIG. 23 is a top plan view of an assembled implant including body portion and end cap shown in place in a vertebra body.
Figure 25:
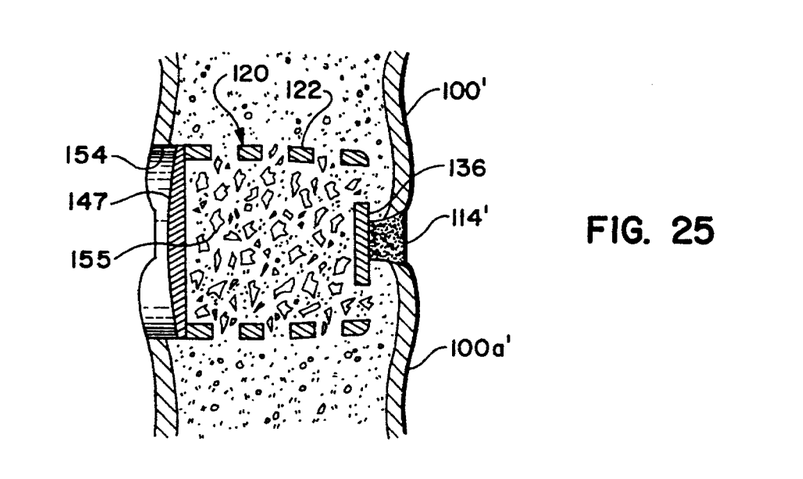
FIG. 25 is a view taken along lines 25—25 of FIG. 23.

Bore 154 is sized to be slightly smaller than the dimensions of body 122. The surgeon inserts the tapered leading end 133 into bore 154. With any suitable hammering mechanism, the surgeon then impacts on the uncapped posterior end 134 to drive the implant 120 into the bore 154 as shown in FIGS. 23 and 25. The tapers $A_7$ and $A_8$ (FIGS. 16 and 22) and the rounded corners on leading end 133 assist in the insertion.

With the implant fully inserted, the surgeon fills the chamber 132 with graft medium 155 (again, preferably bone chips), the surgeon then installs the polyethylene posterior cap 147 to cover posterior end 134 and provide a non-abrasive surface opposing the epidura.

The implant 120 of FIGS. 14–25 greatly enhances the depth of insertion into opposing vertebrae 100', 100a' through a posterior approach. Namely, an oval bore 154 can be formed having a height, $H_2$ (see FIG. 24) equal to about three times the diameter of bores 102 described in previous embodiments. This added depth directly into the bone material of the vertebra body 100', 100a' increases the surface area available for grafting to thereby enhance the probability of a successful graft. Also, the increased depth into each of the vertebra bodies provides increased surface to prevent relative rotation of the opposing vertebrae 100', 100a' about the axis of the spine.

The side walls 124, 126 of the implant do not have openings and, therefore prevent disk material from penetrating into the chamber and thereby interfering with the bone fusion. The implant 120 is sized for the upper and lower openings 133 to be located completely above and below, respectively, the disk layer 114'. Also, plate 136 on end 133 is sized to be about the thickness of layer 114' (or slightly greater) to prevent disk material from entering the interior 132 of implant 120. Openings 138 are positioned to oppose only bone of vertebra 100', 100a'.

H. Additional Alternative Embodiments

Figure 26:
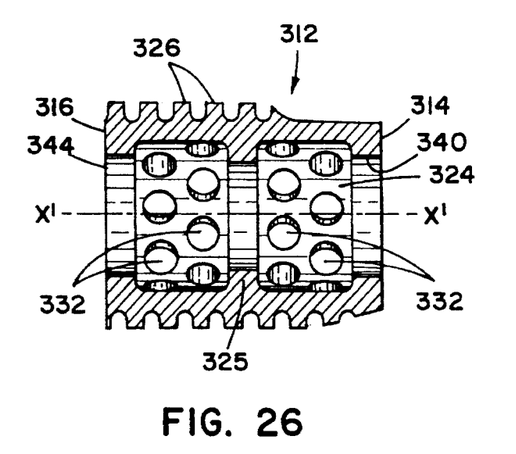
FIG. 26 is a cross-sectional view taken along a longitudinal axis of an alternative embodiment of the present invention.

FIGS. 26–29 show additional alternative embodiments of the present invention. FIG. 26 shows an implant body 312 extending from a leading end 314 to a trailing end 316. The leading end 314 has an axial opening 340 formed therethrough in communication with a body chamber 324. The trailing end 316 has an opening 344 in communication with chamber 324.

A plurality of threads 326 surround the body 312. Further, a plurality of holes 332 are formed through the body.

Figure 27:
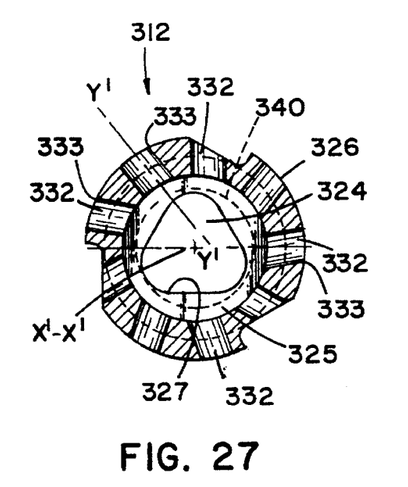
FIG. 27 is a cross-sectional axial view of the embodiment of FIG. 26.

As shown best in FIG. 27, the holes 332 do not extend radially from the longitudinal axis X'-X' of the body 312. Instead, the holes 332 have their axes Y'-Y' disposed radially offset from the longitudinal axis X'-X'. By reason of this structure, an enhanced cutting edge 333 is formed which opposes bone as the body 312 is threaded between the opposing vertebrae. The cutting edge 333 chips away at the bond forcing bone chips to fall through the holes 332 into the chamber 324.

Figure 28:
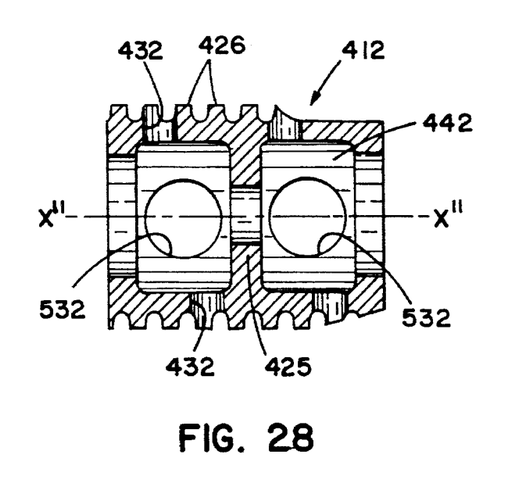
FIG. 28 is a cross-sectional longitudinal view of an additional alternative embodiment of the present invention.
Figure 29:
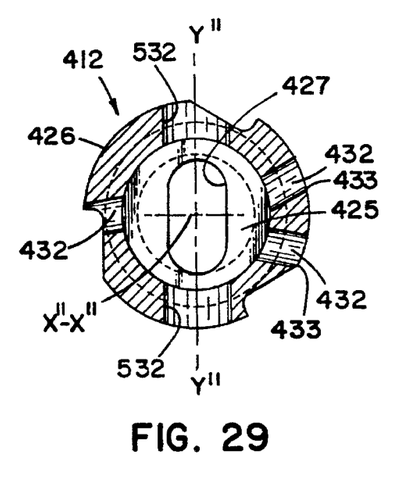
FIG. 29 is a cross-sectional axial view of the embodiment of FIG. 28.

Also shown in FIGS. 26 and 27, a central rib 325 is provided within chamber 324. Rib 325 adds structural integrity to the body 312. Also, as shown best in FIG. 27, a noncircular opening 327 (in the preferred embodiment of FIG. 27, a triangular-shaped opening 327) is provided. Opening 327 may receive the tip of a turning tool (not shown but similar to tool 200 in FIG. 1) which may be inserted within opening 327 to turn the body 312 as it is being threaded between opposing vertebrae. In FIGS. 28 and 29, a body 412 is provide with threads 426. The embodiment of FIGS. 28 and 29 surrounds central chamber 424. A rib 425 is provided within chamber 442. Rib 425 is provided with an oval opening 427 which may receive an oval tool tip (not shown but serving the function of tool tip 200 of FIG. 1). The use of an oval opening 427 in FIG. 29 or a triangular opening 327 in FIG. 27 provides assistance to a surgeon indicating directional alignment of the body 412 with a patient's vertebrae.

In FIGS. 28 and 29, different-sized holes 432 and 532 are shown. Specifically, holes 532 are provided on diametrically opposite sides of implant body 412 and are axially aligned with the longitudinal dimension X"-X" of oval opening 427. The axes between opposing holes 532 defines an axial line Y"-Y" which separates the body into a right and left half (when viewed in FIG. 29). On opposite sides of the line Y"-Y", holes 432 are provided which are smaller in diameter than holes 532. Similar to holes 332 in FIG. 27, holes 432 are provided with their axes offset from the central axes X"-X" of FIG. 29 in order to define cutting edges 433 at the intersection between the holes 432 and the threads 426.

The enlarged holes 532 are provided to align with the opposing vertebrae such that the holes 532 oppose the vertebrae after full insertion of the body 412. Accurate alignment is provided by the surgeon aligning the longitudinal dimension of oval 427 (by operation of an insertion tool not shown) to be in alignment with the vertebrae. When so aligned, the largest holes 532 oppose the vertebrae bone to insure least resistance to bone growth through the body 412. When implanting the body 412, the surgeon will provide a bone slurry filling the implant and the holes 432, 532 and surrounding the body 412. Further, upon implanting the body 412, the bone from the vertebrae is chipped by cutting edges 433 into holes 432. As a result, a solid bone mass is provided through the holes 432 into chamber 442 and surrounding and penetrating the implant body 412.

From the foregoing detailed description of the present invention, it has been shown how the invention has been attained in a preferred embodiment, including alternative embodiments. However, modifications and equivalents of these concepts are intended to be included within the scope of this invention.

What is claimed is:

1. An implant for insertion into a bore formed between opposing vertebrae of an animal's spine, said vertebrae separated by disk material of predetermined dimensions and wherein said bore is generally oval in cross section and extends into said opposing vertebrae and through said disk material, said implant comprising:

a rigid body extending from a leading end to a trailing end spaced apart along a longitudinal axis of said body;
said body having spaced apart side walls and upper and lower walls cooperating to define hollow interior, said upper and lower walls having means for defining openings extending into an interior of said body;

said side walls sized for said implant to be received within said bore with said openings opposing said vertebrae and with said sidewalls sized to oppose said disk material without substantial exposure of disk material to said interior.

2. An implant according to claim 1 wherein said leading end has means for defining axial openings extending through said leading end and exposing said interior, said means dimensioned for said axial openings to oppose said vertebra and with substantial exposure through said axial openings to said interior with said implant received within said bore.

3. An implant according to claim 1 wherein said trailing end is provided with an axial opening therethrough exposing said interior;

said implant further comprising an end cap selected to cover said trailing end axial face.

4. An implant according to claim 3 wherein said end cap is formed of non-abrasive, bio-compatible material.

5. An implant according to claim 1 wherein said upper and lower walls are defined by a plurality of arcuate ribs connecting said side walls with said ribs spaced apart to define said openings.

* * * * *